(12) United States Patent
Maki, Jr.

(10) Patent No.: US 7,942,064 B2
(45) Date of Patent: May 17, 2011

(54) METHOD AND APPARATUS FOR MEASUREMENT OF MECHANICAL CHARACTERISTICS OF A CEMENT SAMPLE

(76) Inventor: Voldi E. Maki, Jr., Austin, TX (US)

(*) Notice: Subject to any disclaimer, the term of this patent is extended or adjusted under 35 U.S.C. 154(b) by 293 days.

(21) Appl. No.: 12/191,363

(22) Filed: Aug. 14, 2008

(65) Prior Publication Data

US 2010/0042342 A1    Feb. 18, 2010

(51) Int. Cl.
G01N 3/00    (2006.01)
(52) U.S. Cl. ........................................... 73/803
(58) Field of Classification Search .............. 73/803, 73/818, 801, 632, 597, 64.42
See application file for complete search history.

(56) References Cited

U.S. PATENT DOCUMENTS

| | | | |
|---|---|---|---|
| 3,474,268 A | 10/1969 | Rudnick | |
| 4,259,868 A | 4/1981 | Rao et al. | |
| 4,341,111 A | 7/1982 | Husar | |
| 4,377,087 A | 3/1983 | Rodot | |
| 4,567,765 A | 2/1986 | Rao et al. | |
| 5,365,778 A | 11/1994 | Sheen et al. | |
| 5,412,990 A | 5/1995 | D'Angelo et al. | |
| 5,595,243 A | 1/1997 | Maki, Jr. et al. | |
| 5,741,971 A | 4/1998 | Lacy | |
| 5,992,223 A | 11/1999 | Sabins et al. | |
| 6,070,465 A | 6/2000 | Maki, Jr. | |
| 6,112,599 A | 9/2000 | Maki, Jr. | |
| 6,192,744 B1 | 2/2001 | Henderson | |
| 6,345,535 B1* | 2/2002 | Sabins et al. | 73/818 |
| 6,412,354 B1 | 7/2002 | Birchak et al. | |
| 6,941,231 B2 | 9/2005 | Zeroug et al. | |
| 6,941,819 B1 | 9/2005 | Maki, Jr. et al. | |
| 7,089,816 B2* | 8/2006 | Hakimuddin | 73/866 |
| 7,191,663 B2 | 3/2007 | Boncan et al. | |
| 7,380,466 B2* | 6/2008 | Deeg | 73/803 |
| 7,677,104 B2* | 3/2010 | Maki et al. | 73/632 |
| 2002/0112540 A1* | 8/2002 | Zeroug et al. | 73/579 |

OTHER PUBLICATIONS

Johannes Vollman et al., "High-Resolution Analysis of the Complex Wave Spectrum in a Cylindrical Shell Containing a Viscoelastic Medium. Part I. Theory and Numerical Results", Journal of Acoustical Society of America 102 (2), Pt. 1, Aug. 1997, p. 896-908.
Johannes Vollman et al., "High-Resolution Analysis of the Complex Wave Spectrum in a Cylindrical Shell Containing a Viscoelastic Medium. Part II. Experimental Results Versus Theory", Journal of Acoustical Society of America 102 (2), Pt. 1, Aug. 1997, p. 909-920.
Alf Puttmer et al., "SPICE Model for Lossy Piezoceramic Transducers", IEEE Transactions on Ultrasonics, Ferroelectrics, and Frequency Control, vol. 44, No. 1, Jan. 1997, p. 60-66.

(Continued)

*Primary Examiner* — Lisa M Caputo
*Assistant Examiner* — Octavia Davis
(74) *Attorney, Agent, or Firm* — Andrew J. Dillon; Dillon & Yudell LLP

(57) ABSTRACT

A system for non-destructively measuring the strength of a cement slurry sample includes an elongate sample container for receiving a cement slurry sample. The elongate sample container has a mass mounted at its first end. A transducer mounted at a second end of the elongate sample container vibrates the elongate sample container and mass. The elongate sample container, mass and transducer have a known resonance. The system calculates the strength of a tested cement slurry within the elongate sample container as a function of variation in resonance of the elongate sample container, mass and transducer.

20 Claims, 6 Drawing Sheets

OTHER PUBLICATIONS

W. Marshall Leach, Jr., "Controllerd-Source Analogous Circuits and SPICE Models for Piezoelectric Transducers", IEEE Transactions on Ultrasonics, Ferroelectrics, and Frequency Control, vol. 41, No. 1, Jan. 1994, p. 60-66.

Steven A, Morris et al., "Implementation of Mason's Model on Circuit Analysis Programs", IEEE Transactions on Ultrasonics, Ferroelectrics, and Frequency Control, vol. UFFC-33, No. 3, May 1986, p. 295-298.

F. Simonetti et al., "A Guided Wave Technique for the Characterization of Highly Attenuative Viscoelastic Materials", Journal of Acoustical Society of America 114 (1), Jul. 2003, p. 158-165.

Thomas K. Vogt et al., "Measurement of the Material Properties of Viscous Liquids Using Ultrasonic Guided Waves", IEEE Transactions on Ultrasonics, Ferroelectrics, and Frequency Control, vol. 51, No. 6, Jun. 2004, p. 737-747.

* cited by examiner

METHOD AND APPARATUS FOR MEASUREMENT OF MECHANICAL CHARACTERISTICS OF A CEMENT SAMPLE

BACKGROUND OF THE INVENTION

1. Field of the Invention

The present invention relates in general to methods and apparatus for testing material samples which are initially fluid but which may change to a solid during testing. More specifically, the present invention relates to method and apparatus for determining the gel strength and compressive strength of a cement slurry sample.

2. Description of the Prior Art

Cement is utilized at different times during the drilling, completion, and repair of oil and gas wells to bond the well casing to the well bore. This technique is utilized to seal off any flow of fluids or gas along the length of the casing. The cement utilized is formulated specifically for the temperature and pressure conditions found in the well being cemented. Because of the wide range of conditions present in typical oil wells there are a wide range of diverse cement formulations utilized in this cementing procedure. In order to ensure proper cementing within the well the cement utilized is typically tested in a laboratory utilizing the specific conditions believed to be present in a particular well. Multiple measurement systems are described, for example, in U.S. Pat. No. 4,259,868 issued to Rao, et al.; U.S. Pat. No. 4,567,765 to Rao, et al.; U.S. Pat. No. 5,412,990 to D'Angelo, et al.; and U.S. Pat. No. 5,992,223 to Sabins, et al.

A primary requirement in such operations is that the cement slurry remain fluid for a period long enough to permit the slurry to be pumped to desired locations within the well. A high temperature-high pressure consistometer is often utilized to measure the thickness or consistency of the cement during the pumping operation. Once in place the cement must develop adequate gel strength to prevent fluid or gas movement before the cement develops compressive strength. Eventually, it is necessary to know that adequate compressive strength has developed before beginning certain other operations within an oil well. An ultrasonic cement analyzer may be utilized to measure the gel strength and the compressive strength of the cement as it cures. Previous versions of devices utilized to obtain these measurements typically utilized one or two acoustic transducers to measure the sound velocity within the cement to obtain the compressive strength or the amplitude of the signal through the cement in order to obtain the gel strength.

These prior art devices typically utilized relatively large samples of cement contained within a pressure vessel. After the cement has set and the test is complete the pressure vessel would then be disconnected from the high pressure fluid source and electronics to allow its removal from the housing which contains the electronics, pressure source and heat source. These pressure vessels, typically weighing 20 lbs. or more, would then be taken to a large bench vice to allow removal of both the top and bottom plugs from the pressure vessel. The cement sample may then be driven from the pressure vessel. Once the cement has been removed grease is typically applied to all interior surfaces of the pressure vessel before filling the pressure vessel with a subsequent cement sample. This test equipment does not lend itself to affordability or portability in view of the massive pressure vessels required. Additionally, this test equipment is quite expensive.

SUMMARY OF THE INVENTION

The present invention describes an alternate method and apparatus for obtaining the gel strength and compressive strength of a cement slurry. This technique provides a comparable accuracy with a much smaller and less expensive test instrument, making the measurement much more widely available within the industry. Increasing the availability of testing will greatly improve the quality of the typical cementing job within an oil well by increasing access to the testing of the cement slurry prior to placing the cement within the well.

A cement sample, in accordance with the present invention, is placed within a small tube within pressure vessel. The tube includes a steel plug at a first end and the opposite end thereof is connected to a plug threaded into a pressure vessel. The tube is then attached to the plug through a diaphragm, which allows a piezoelectric ceramic device outside of the pressure vessel to vibrate the tube across a range of frequencies. This continuous vibration is in direct contrast to the prior art wherein short acoustic pulses were typically utilized to characterize the cement slurry and wherein the cement slurry typically filled a large pressure vessel. A steel weight, either integral with the tube or attached to one end of the tube opposite piezoelectric ceramic element, can be utilized to trap the acoustic energy generated by the piezoelectric ceramic element within the tube. The electrical admittance of the piezoelectric ceramic element thereafter produces a strong indication of the mechanical characteristics of the tube and the cement material within the tube. The electrical admittance may then be utilized to determine both the gel strength and compressive strength of the cement slurry contained within the tube under appropriate signal analysis. Upon completion of the test the cement sample is simply removed by disconnecting the plug from the pressure vessel so that the tube and cement sample may be removed. The pressure vessel typically contains water, a temperature sensor and a fluid inlet to provide the appropriate pressure. A cement sample contained within the tube may be thereafter simply removed from the tube or the tube may be replaced for subsequent tests. No specialized heavy equipment is required to open the pressure vessel or remove the cement sample, making the present test much more amenable to field testing than previously known devices.

BRIEF DESCRIPTION OF THE DRAWINGS

The novel features believed characteristic of the invention are set forth in the appended claims. However, the invention, as well as a preferred mode of use, will best be understood by reference to the following detailed description of an illustrative embodiment when read in conjunction with the accompanying drawings, wherein:

DETAILED DESCRIPTION OF THE PREFERRED EMBODIMENT

Figure 1:
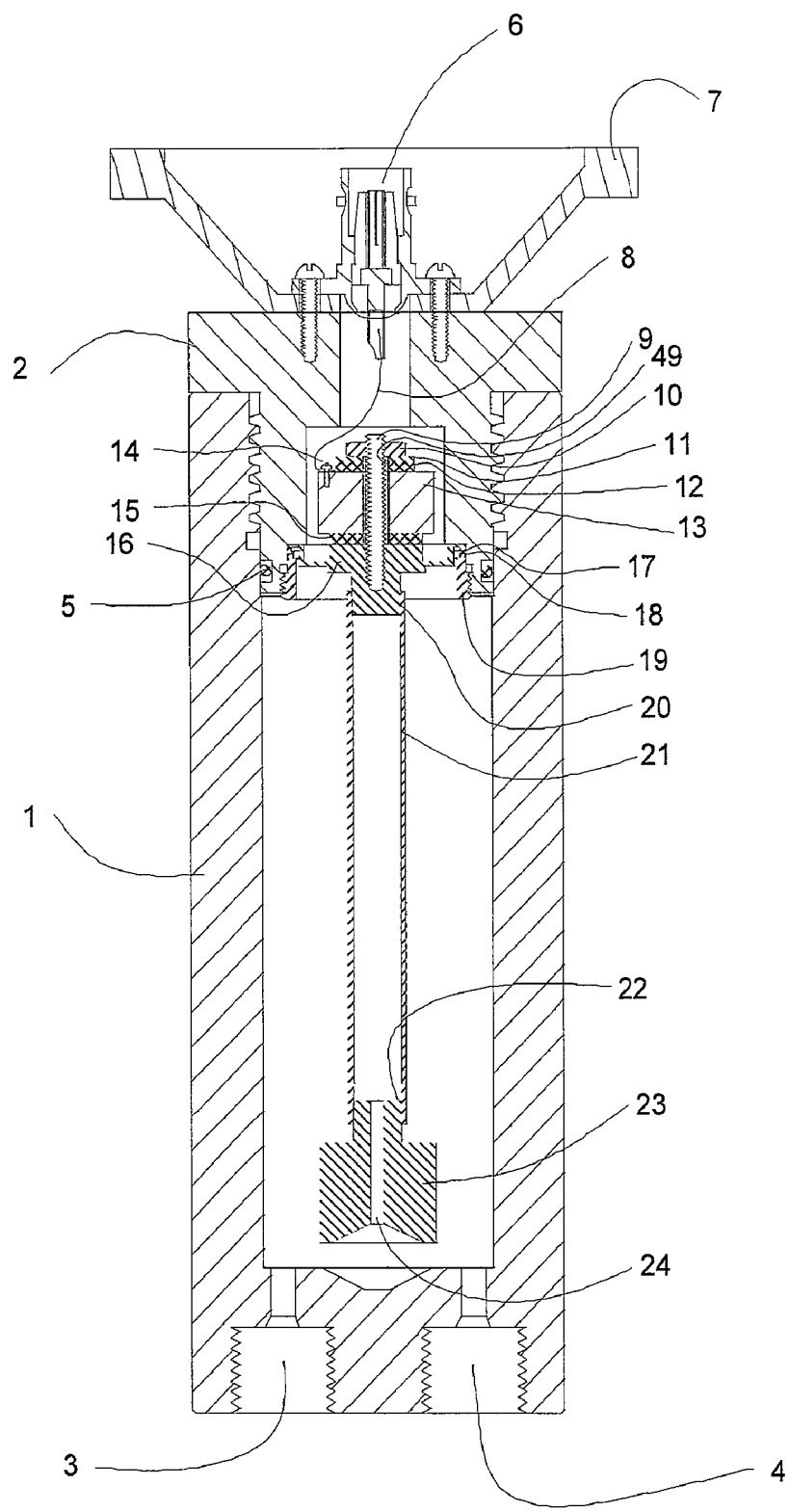
FIG. 1 is a sectional view of the test system of the present invention depicting the sample tube within a pressure vessel.

With reference now to the figures and in particular with reference to FIG. 1 there is depicted a sectional view of the test system of the present invention. As illustrated, the test system includes a pressure vessel 1, which, in the depicted embodiment, typically contains water. An end plug 2 may be removed to permit placement of cement slurry sample for testing or for removal of the cured cement subsequent to testing.

Depicted at the bottom of pressure vessel 1 are ports 3 and 4, which permit placement of a temperature sensor and allow pressurized fluid to be added or removed from pressure vessel 1 in order to obtain the appropriate temperature and pressure required to match conditions within a particular well. As depicted, pressure vessel 1 is generally disposed in a vertical position so that when end plug 2 has been removed the pressure vessel may be filled with water or other appropriate fluid. Once end plug 2 has been replaced, pressure vessel 1 may, as those having ordinary skill in the art will appreciate upon reference to the foregoing, be placed either in a horizontal or vertical position for testing. In the depicted embodiment of the present invention horizontal placement is preferred to eliminate any effects of free water formation within the cement slurry.

As illustrated, a flange 7 is mounted to the upper surface of end plug 2 utilizing bolts of sufficient strength, which also may be utilized to mount electrical connector 6. Flange 7, as those having ordinary skill in the art will appreciate, provides a suitable grip to permit hand removal of end plug 7 and also allows end plug 7 to stand vertically when placing a cement slurry sample into testing tube 21, when testing tube 21 is inverted, as will be described herein.

As depicted, a port 24 is provided at the lower end of testing tube 21. An end mass 23 is also attached to testing tube 21 having a tapered fit 22 within testing tube 21. Of course, those having ordinary skilled merit will appreciate that mass 23 may be integrally formed with testing tube 21 in an alternate embodiment. In the depicted embodiment of the present invention a small amount of vacuum grease is typically placed on mass 23 to lubricate and seal the mating surfaces of mass 23 and testing tube 21. Thus, as testing tube 21 is forced into a mating relationship with mass 23, a self-holding contact can be achieved.

An identical procedure may be utilized on the upper end of testing tube 21, as indicated at reference numeral 20. At this point testing tube 21 is attached to an acoustic driving fitting 16. Acoustic driver fitting 16 is preferably sealed to end plug 2 utilizing an O-ring 17, a torque isolation ring 18 and a threaded retaining ring 19. In alternate embodiments the acoustic driver fitting may simply be welded to the end plug so as to eliminate any possibility of seal failure.

A piezoelectric ceramic element 15 is then placed against the opposite side of the driver fitting. A steel mass 13 is then placed against the opposite side of piezoelectric ceramic element 15. This steel mass 13 then acts as a positive electrode for the piezoelectric ceramic element 15 while the driver fitting 16 acts as the ground electrode. Steel mass 13 is then connected to the center electrode of an electrical connector 6 utilizing a wire attached at reference numeral 14, utilizing a small machine screw.

A ground connection is then made through the metal body of end plug 2 and a ceramic washer 12 may then be placed against the opposite face of steel mass 13. A steel washer 11 and a nut 10 are then placed on threaded rod 9, which passes through driver fitting 16. An insulating sleeve 49 then covers threaded rod 9. Tightening nut 10 then clamps all components tightly together as a single mechanical entity.

The relatively high mass of end mass 23 and steel mass 13 cause a major resonance at the half wave length as determined by the speed of sound within testing tube 21, based upon its length. This resonance may be simply measured by detecting the electrical admittance of piezoelectric ceramic element 15. Thus, as the cement slurry cures, this and other resonances will change and develop within the described test structure.

Figure 2:
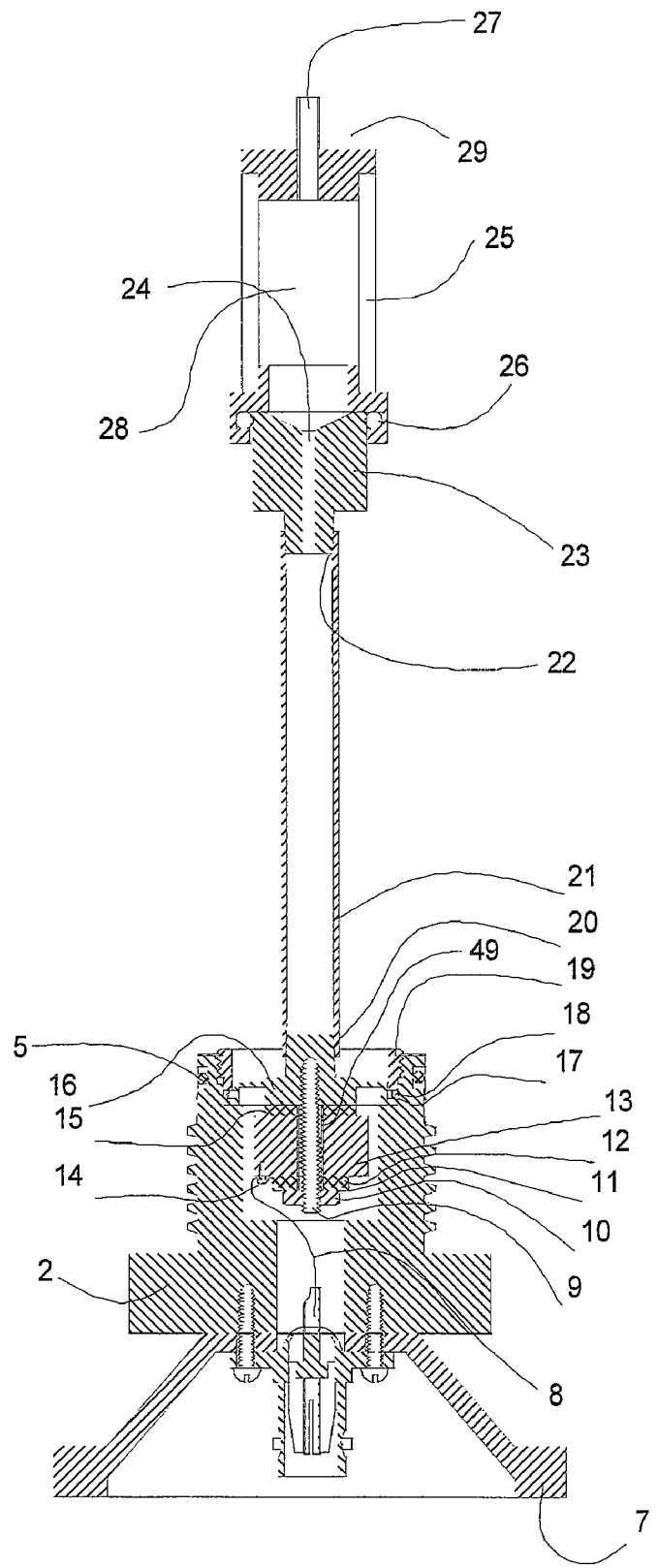
FIG. 2 is a sectional view depicting the sample tube and sensor system configured for filling with cement slurry.

Referring now to FIG. 2 the manner in which testing tube 21 is filled is depicted within the sectional view thereof. As illustrated, end plug 2 is placed on a bench with flange 7 resting on the bench. A small vessel 28 is then placed on end mass 23. An O-ring seal 26 may be utilized to seal the vessel to end mass 23. A plastic pipette may then be utilized to place a quantity of cement slurry through port 27 to fill approximately one-third of the volume of vessel 28. In the depicted embodiment of the present invention side walls 25 of vessel 28 are preferably transparent, in order to make the fill amount relatively easy to determine.

Next, a hand vacuum pump (not shown) is connected to port 27 and a vacuum is pulled, removing, the air within testing tube 21 and vessel 28. This vacuum also removes most of the air trapped within the cement slurry. Releasing the vacuum thereafter allows atmospheric pressure to push the cement slurry through port 24 into the volume of testing tube 21. Vacuum may be applied several times in order to be certain that there is no air left in testing tube 21. Once testing tube 21 has been filled, vessel 28 can be removed. Port 24 is of sufficiently small diameter that cement will generally not flow from testing tube 21 even when testing tube 21 has been inverted. However, a small semi-permeable cap may also be place on end mass 23 to eliminate any loss of cement into the pressure vessel but to allow fluid within the pressure vessel to pressurize the cement sample and supply any water absorbed into the cement as it cures.

Figure 3A:
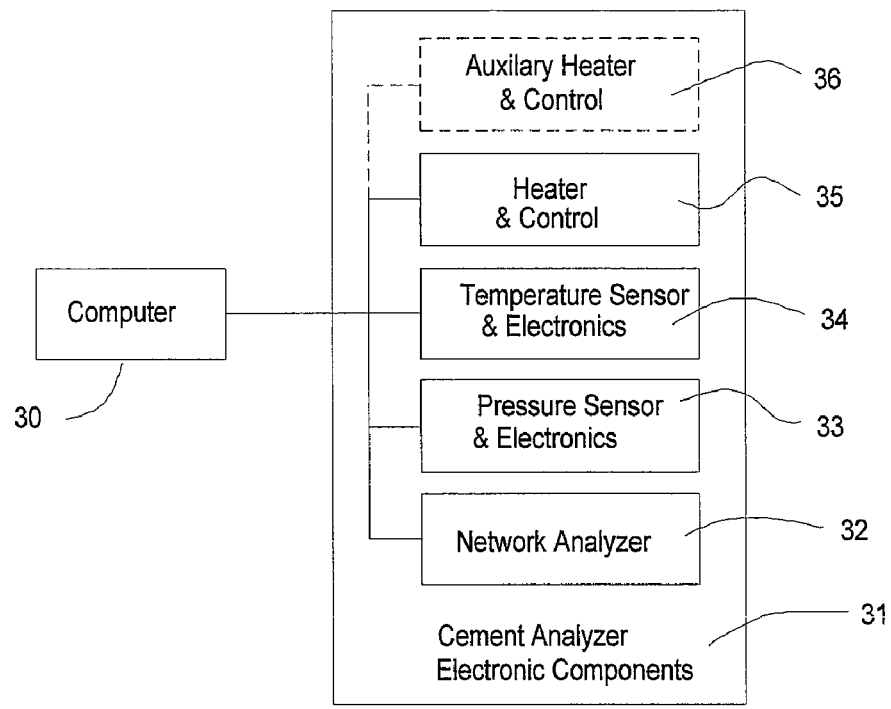
FIGS. 3A and 3B are high level block diagrams of the electrical and hydraulic components of the test system of the present invention.
Figure 3B:
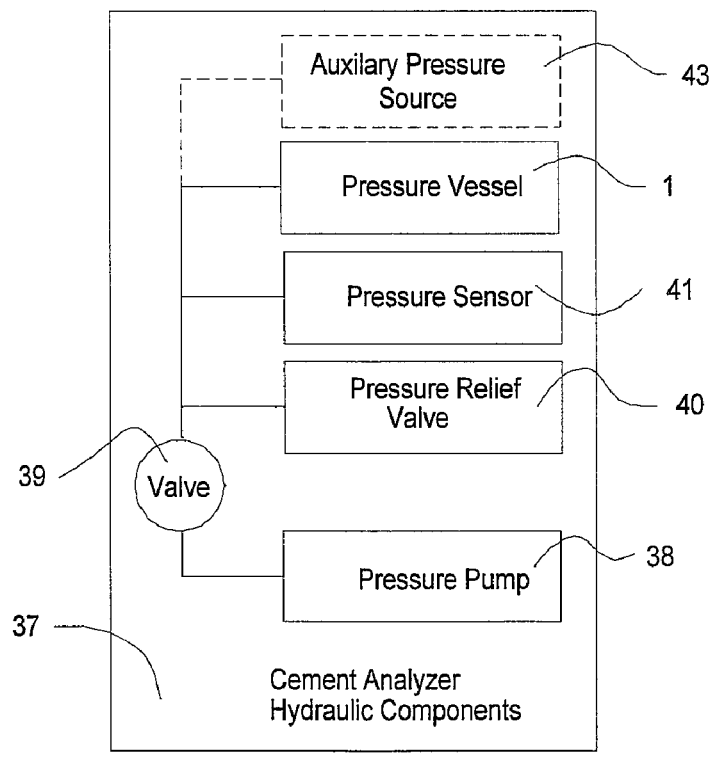

A high level block diagram of the electronic and hydraulic components of the test system of the present invention are depicted within FIGS. 3A and 3B. As illustrated in FIG. 3A, electronic components 31 include a computer 30 for providing timing and control logic in order to produce a proper heat cycle and monitor the pressure within the pressure vessel. Computer 30 also processes the admittance of piezoelectric ceramic element 15 (See FIG. 1) as a function of frequency. The computer 30 then applies processing functions to calculate the gel strength and compressive strength of the cement slurry as it cures. These functions are derived from experimental data. A heater control 35 is included within electric components 31 and is utilized to modulate the line voltage, which provides an appropriate current to an electronic heater element (not shown) surrounding pressure vessel 1. (See FIG. 1) Temperature sensor 34 is preferably a thermocouple within the cell, the output voltage of which is converted to a digital representation of the temperature. Pressure sensor electronics 33 are provided in order to convert the output of a strain gauge pressure sensor to a digital value. An auxiliary heater 36 and controller may be utilized to heat a separate a reservoir to compensate for fluid take-up as the cement cures. This fluid take-up may also be compensated by a slight increase in the temperature within pressure vessel 1.

Network analyzer 32 is also depicted. The network analyzer 32 may be a suitable device such an AD5934 made by Analog Devices, which contains a complete network analyzer or separate signal generator and envelope detector in order to measure the input current of the piezoelectric ceramic element. In either case, the electrical admittance of piezoelectric ceramic element 15 at a range of frequencies can then be utilized to evaluate the gel strength and compressive strength of the cement slurry.

Depicted within FIG. 3B are the hydraulic components 37 of the test system of the present invention. As illustrated, a pressure pump 38 is provided. In the depicted embodiment of the present invention pressure pump 38 is preferably a manual screw piston pump. A valve 39 is provided in order to isolate pump 38 from pressure vessel 1 once the desired pressure has been achieved. A pressure relief valve 40 is provided to allow excess fluid to exit the pressure vessel as the pressure vessel is heated to a proper temperature. Pressure sensor 41 may be utilized to monitor the pressure within pressure vessel 1. A small auxiliary pressure vessel 43, preferably having a small fraction of the volume of pressure vessel 1 may also be added to produce the fluid volume change which occurs as the cement cures. By heating this small volume the pressure may be controlled in the system automatically without an otherwise required slight increase in the sample temperature. No additional pumping devices are required to control the pressure during a test.

In operation, end plug 2 is placed in pressure vessel 1 and the fluid therein is pressurized. Computer 30 then controls the heating of the cement slurry, at a proper rate, to the desired temperature. Computer 30 also controls the acquisition of the electrical admittance of piezoelectric ceramic element 15. The admittance of the piezoelectric ceramic element 15 indicates the capacitance of the piezoelectric ceramic element and the mechanical resonances of testing tube 21 and the associated components, including the cement slurry contained therein.

Figure 4:
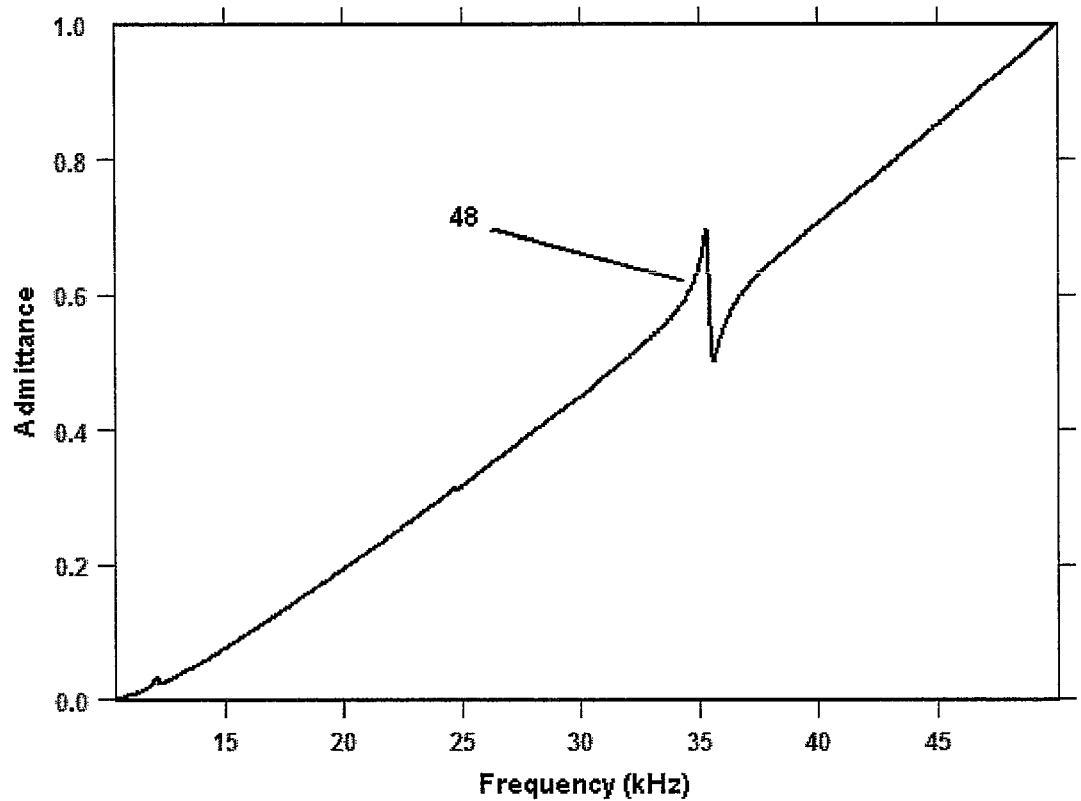
FIG. 4 is a graphically depiction of variations in the admittance of the piezoelectric ceramic device at various frequencies.

Referring now to FIG. 4 there is depicted a typical signal generated by the test system of the present invention. As illustrated, when the admittance of piezoelectric ceramic element 15 is graphed against the frequency, the upward slope indicates the capacitance of piezoelectric ceramic element 15. The inflection in admittance at reference numeral 48 indicates that a resonance of testing tube 21 and the associated end masses has occurred. As the cement begins to develop gel strength it begins to reduce the ability of the walls of testing tube 21 to move, causing the depicted inflection at reference numerals 48 to decrease in magnitude.

Figure 5A:
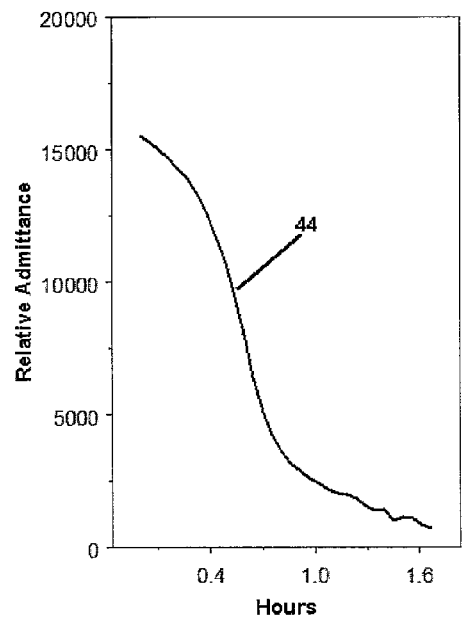
FIGS. 5A-5D depict measured data, computed gel strength and computed compressive strength obtained utilizing the test system of the present invention.

With reference now to FIG. 5A it can be seen at trace 44 that the magnitude of the inflection decreases as the gel strength increases. The change in the mechanical character of testing tube 21, which is filled with cement, as indicated by the admittance of piezoelectric ceramic element 15, may be utilized to directly indicate the gel strength of the cement sample therein.

Figure 5B:
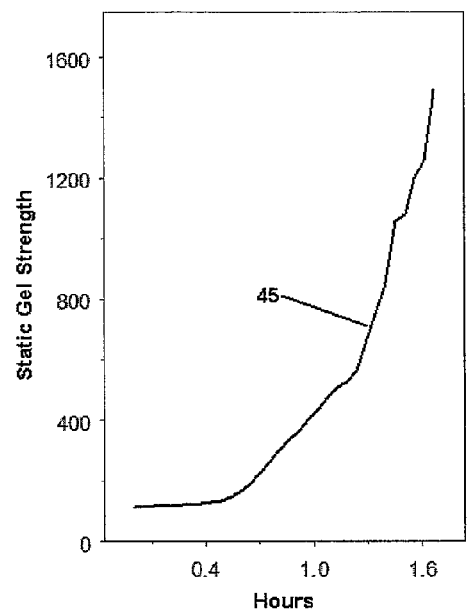
Figure 5C:
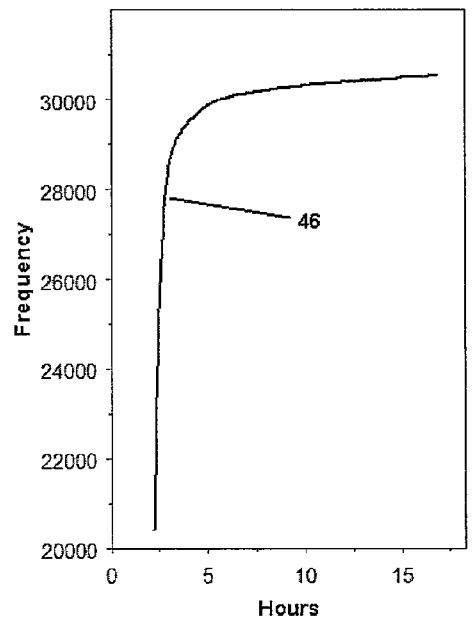
Figure 5D:
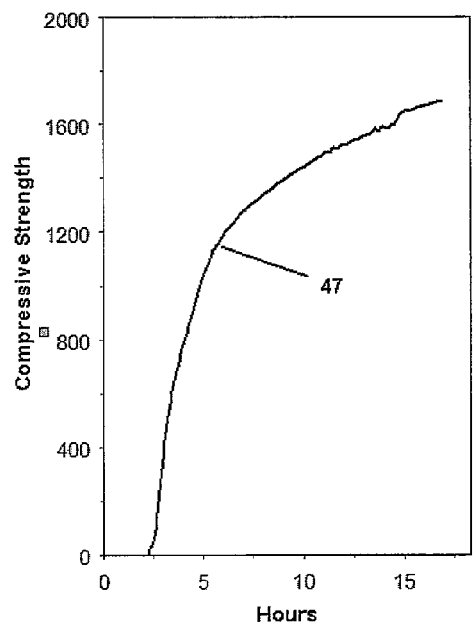

Referring to FIG. 5B trace 45 shows gel strength development in another cement sample at a slightly lower temperature after application of the appropriate function to the admittance data. This function can be developed utilizing regression analysis on data from physical measurement of the slurry gel strength and admittance data. As the cement slurry hydrates further, another inflection with a changing frequency indicates the development of compressive strength as is shown within trace 46 with FIG. 5C. This inflection is indicative of the compressive strength of the cement slurry. Again, a regression analysis is utilized to develop the function utilized to translate the frequency of the inflection in admittance to compressive strength, as depicted within trace 47 of FIG. 5D.

Figure 6:
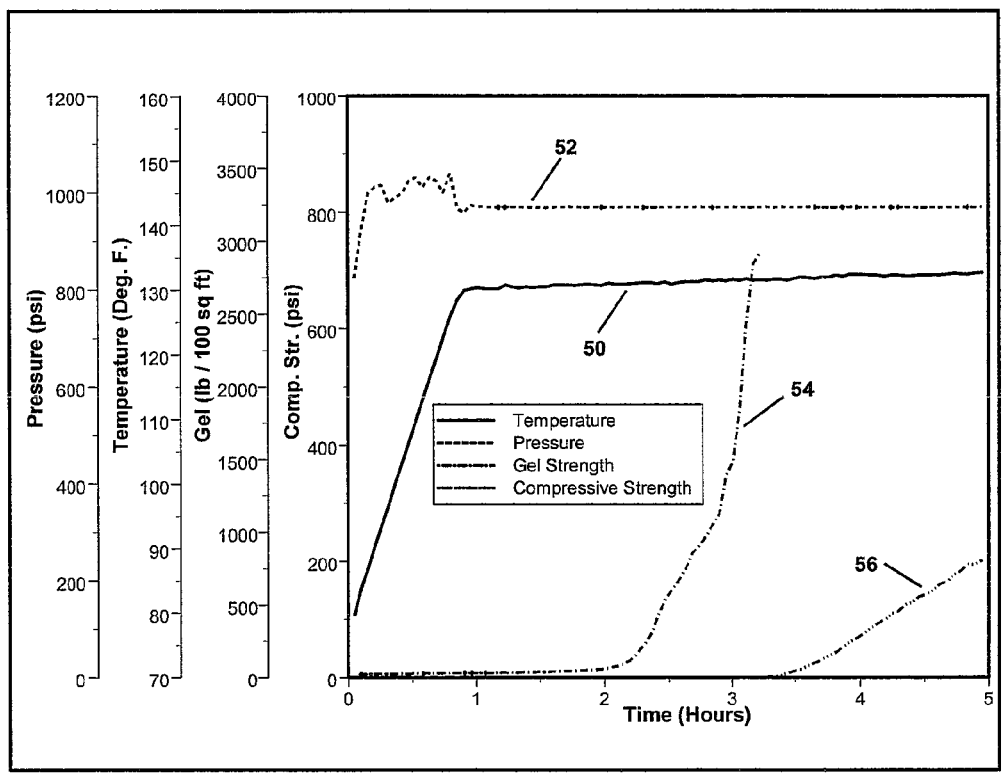
FIG. 6 depicts the processed output of the test system of the present invention.

Finally, referring to FIG. 6, the pressure, temperature, gel strength, and compressive strength of a single cement slurry sample are depicted within a single graph. Temperature 50 increases at a specified rate to a set point temperature. Once the desired temperature has been achieved the temperature is modified slightly to compensate for any volume changes of the slurry within the test system once the pressure 52, decreases below a set value, as determined by the pressure relief valve. The pressure within the test system then remains constant while the temperature is allowed to change a small amount while the slurry sets. Gel strength 54 is then indicated as is compressive strength 56 as the cement slurry sets within the test system of the present invention.

What is claimed is:

1. A system for non-destructively measuring the strength of a cement slurry sample comprising:
   an elongate sample container for receiving a cement slurry sample, said elongate sample container having a mass mounted at a first end thereof;
   a transducer mounted at a second end of said elongate sample container for vibrating said elongate sample container and mass, wherein said elongate sample container, mass and transducer have a known resonance; and
   means for calculating the strength of a tested cement slurry within said elongate sample container as a function of variation in resonance of said elongate sample container, mass and transducer.

2. The system as claimed in claim 1, including:
   a pressure vessel for containing said elongate sample container.

3. The system as claimed in claim 2, including:
   means for introducing a fluid into said pressure vessel.

4. The system as claimed in claim 3, including:
   means for heating said fluid in said pressure vessel.

5. The system as claimed in claim 1, wherein said transducer includes a piezoelectric element.

6. The system as claimed in claim 5, wherein said piezoelectric element includes a ceramic element.

7. The system as claimed in claim 1, wherein said means for calculating includes a computer.

8. The system as claimed in claim 1, wherein said elongated sample container includes a cylindrical tube.

9. The system as claimed in claim 8, wherein said mass is removably mounted to said cylindrical tube.

10. The system as claimed in claim 1, including:
    means for pressurizing a fluid in said pressure vessel; and,
    means for heating said fluid in said pressure vessel.

11. A method of non-destructively measuring the strength of a cement slurry sample comprising:
    introducing a cement slurry sample into an elongate sample container, said elongate sample container having a mass mounted at a first end thereof, said elongated sample container and mass having a known resonance;
    vibrating said elongate sample container and mass with said cement slurry sample contained in said elongate sample container; and
    means for calculating the strength of a tested cement slurry within said elongate sample container as a function of variation in resonance of said elongate sample container and mass with said cement slurry sample contained in said elongate sample container.

12. The method as claimed in claim 11, including:
    placing said elongate sample container in a pressure vessel.

13. The method as claimed in claim 12, including:
    introducing a fluid into said pressure vessel.

14. The method as claimed in claim 13, including:
    heating said fluid in said pressure vessel.

15. The method as claimed in claim 11, wherein said vibrating includes:
    mounting a transducer to a second end of said elongate sample container.

16. The method as claimed in claim 15, wherein said transducer includes a piezoelectric element.

17. The method as claimed in claim 11, wherein said elongated sample container includes a cylindrical tube.

18. The method as claimed in claim 17, wherein said mass is removably mounted to said cylindrical tube.

19. The method as claimed in claim 11, including:
    pressurizing a fluid in said pressure vessel; and,
    heating said fluid in said pressure vessel.

20. The method as claimed in claim 11, including:
    pressurizing said elongate sample container; and,
    heating said elongate sample container.

* * * * *